United States Patent [19]

Dong et al.

[11] Patent Number: 4,611,077
[45] Date of Patent: Sep. 9, 1986

[54] INCREASING ENANTIOMERIC SELECTIVITY IN CHIRAL CYANOHYDRINATION

[75] Inventors: Walter Dong, Houston, Tex.; Donald W. Stoutamire, Modesto, Calif.

[73] Assignee: Shell Oil Company, Houston, Tex.

[21] Appl. No.: 749,619

[22] Filed: Jun. 26, 1985

[51] Int. Cl.$^4$ ............................................. C07C 121/75
[52] U.S. Cl. ...................................... 558/351; 549/58; 549/75; 549/426; 549/491
[58] Field of Search ................ 260/465 F; 549/58, 75, 549/426, 491; 558/351

[56] References Cited

FOREIGN PATENT DOCUMENTS 109681 5/1984 European Pat. Off. .
132392 1/1985 European Pat. Off. .
135691 4/1985 European Pat. Off. .
58-29757 2/1983 Japan .

OTHER PUBLICATIONS

Oku, J. et al., *J.C.S. Chem. Comm.*, pp. 229–230 (1981).
Oku, J. et al., *Makromol. Chem.*, 183, pp. 579–586 (1982).
Oku, J., *Kagaku Kogyo*, 32 (11), pp. 1134–1136 (62–64), Nov. 1981, and translation.

*Primary Examiner*—Dolph H. Torrence

[57] ABSTRACT

Enantiomeric selectivity is increased in chiral cyanohydrination of an aromatic aldehyde using a chiral cyclo(phenylalanylhistidine) catalyst by treating the (recycle) aldehyde to remove catalyst poisons or impurities which adversely effect enantiomeric selectivity.

11 Claims, No Drawings

INCREASING ENANTIOMERIC SELECTIVITY IN CHIRAL CYANOHYDRINATION

BACKGROUND OF THE INVENTION

1. Field of the Invention

The present invention is directed to a process for chiral cyanohydrination in which catalyst poisons or impurities are removed to increase enantiomeric selectivity.

2. Description of the Prior Art

Chiral cyanohydrins, including optically-active alpha-hydroxy benzonitriles are known in the art and are of interest, per se, and as intermediates, e.g. to esters. In pyrethroid esters, those having an alpha-S-alpha-hydroxynitrile moiety coupled with the appropriate pyrethroid acid usually have the highest pesticidal activity. However, such alpha-S-alpha-hydroxynitriles have not been particularly easy to obtain in the past because they were usually prepared by resolution.

Asymmetric synthesis of R-mandelonitrile by addition of hydrogen cyanide to benzaldehyde in the presence of a synthetic dipeptide catalyst is known in the art, as in Oku, Jun-ichi and Shohei Inoue, *J.C.S. Chem. Comm.*, pages 229–230 (1981), and other Oku publications where, e.g., cyclo(L-phenylalanyl-L-histidine) containing ½ mole of water of crystallization was used. However, it has been found by applicants that the process of chiral cyanohydrination with cyclo(L-phenylalanyl-L-histidine) or cyclo(D-phenylalanyl-D-histidine) is not necessarily satisfactory or optimal for the preparation of chiral cyanohydrins because of problems with the purity of the aldehyde used for the process associated with poisoning of the catalyst and competitive non-chiral reactions. Applicants have now found that these problems can be solved by the present invention while also increasing further the enantiomeric selectivity of the chiral cyanohydrin product.

SUMMARY OF THE INVENTION

The present invention is directed to a process of preparing a chiral aromatic cyanohydrin (optically-active alpha-hydroxynitrile) or a mixture enantiomerically enriched therein which comprises treating a aromatic aldehyde with hydrogen cyanide or a generator thereof in the presence of an inert, aprotic solvent, a cyclo(D-phenylalanyl-D-histidine) or cyclo(L-phenylalanyl-L-histidine) dipeptide as a catalyst and pretreating the aldehyde or solution thereof in the solvent to remove catalyst poisons or impurities that adversely affect enantiomeric selectivity.

Such treatment is particularly important when the catalyst, solvent streams, or a minor amount of product chiral cyanohydrin is recycled in either a continuous or batch chiral cyanohydrination process because poisons or other adverse impurities would otherwise continue to build up in the reaction system resulting in a continued decline in enantiomeric selectivity over the time of operation of the process. Removal of the undesirable materals in the aldehyde feed results in increased enantiomeric selectivity and the prevention of significant decline thereof over the operation of the process, particularly when using recycled catalyst, solvent or product of chiral cyanohydrination.

Basic nitrogen compounds were found to be poisonous to and/or competitive with the chiral cyclo(phenylalanyl-histidine) catalyst used in chiral cyanohydrination resulting in reduced enantiomeric selectivity. Amines are the chief basic nitrogen compounds which may be present in the aldehyde reactant. Carboxylic acids also are undesirable materials, particularly when basic nitrogen compounds, such as amines are also present.

Thus, the process of the present invention includes treating the aldehyde, or a solution thereof, in a solvent to remove catalyst poisons or impurities that adversely effect enantiomeric selectivity such as amines and optionally carboxylic acids.

Residual amines are readily removed by treating the aldehyde or a solution thereof with an acid or acidic acting material, which will neutralize and, preferably, remove the amines in an aldehyde reactant of the process. Suitable acid or acidic acting materials include those materials having strong acidity and being essentially insoluble in the organic phase being treated, acidic clays, such as acidic silicates, aluminates or synthetic acidifed clays, acidic cation exchange resins, e.g., sulfonic acid cation exchange resins, including of the Dowex and Amberlite types, and mineral acids, such as hydrochloric, sulfuric or phosphoric acids.

Since carboxylic acid impurities are a problem, particularly in the presence of basic nitrogen compounds, such as amines, it can be desirable to treat the aldehyde or a solution thereof with a base or basic acting substance, which will neutralize and, preferably, remove the carboxylic acid impurities in the aldehyde of the process. Suitable bases or basic acting materials, including the alkali metal and alkaline earth metal hydroxides. Examples of such alkaline materials include the following hydroxides: sodium hydroxide, potassium hydroxide, lithium hydroxide, calcium hydroxide, magnesium hydroxide, barium hydroxide, and the like. A source of alkalinity (basic acting substance) can also comprise the various anion exchange resins which are charged with soluble anions such as halides, e.g., chloride, bromide, fluoride, nitrate, sulfate, and the like, Examples of suitable base exchange resins are: amination products of chloromethylated styrene-divinylbenzene copolymers marketed by Rohm & Haas as "Amberlite IRA-400" and "IRA-401" made by reacting formaldehyde, malamine and diethylenetriamine; resins having quaternary ammonium groups linked to polystyrene that has been cross-linked with divinyl benzene marketed by Dow Chemical Company as "Dowex-1" and "Dowex-2", and resins having polyalkylamine groups linked to a polysytrenedivinyl benzene matrix marketed by Dow Chemical Company as "Dowex-3".

Some treatments, including use of a high vacuum spinning distillation band column, adsorption, and the like, can remove the amines, and acids. For example, Florisil (magnesium silicate), molecular sieves and other similar conventional adsorbents are useful.

It may be advantageous to treat the aldehyde or a solution thereof with more than one of the above kinds of materials in series or to treat the aldehyde or a solution thereof successively with the same kind of material for optional removal of catalyst poisons or other detrimental impurities that adversely effect enantiomeric selectivity in this chiral cyanohydrination process.

The amount of treating agent used is dependent on the amount of undesirable material(s) present in the aldehyde feed and is conventionally determinable by one of ordinary skill in the art.

In one embodiment, the present invention is directed to a process for the preparation of chiral aromatic cyanohydrins (optically-active alpha-hydroxynitriles) or a mixture enantiomerically enriched therein which comprises treating the corresponding aldehyde with a source of hydrogen cyanide in a substantially water-immiscible, aprotic solvent and in the presence of a cyclo(D-phenylalanyl-D-histidine) or cyclo(L-phenylalanyl-L-histidine) dipeptide as a catalyst and a step of pretreating the aldehyde or a solution thereof in the solvent to remove catalyst poisons or impurities that adversely effect enantiomeric selectivity. These products of formula I are then optically-active, optionally-substituted alpha-cyano alcohols or a mixture enantiomerically enriched in such an alcohol.

The chiral aromatic cyanohydrin products include those of formula I

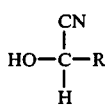

wherein R is an optionally-substituted carboxyclic or an O- or S-heterocyclic aromatic group containing up to 20 carbon atoms. Examples of carbocyclic aryl groups include phenyl, 1-naphthyl, 2-naphthyl and 2-anthryl groups. O- or S-heterocyclic aromatic groups include those derived from hetero-aromatic compounds defined in Kirk-Othmer, "Encyclopedia of Chemical Technology", Second Edition, Volume 2 (1963), page 702: obtained by replacement of one or more carbon atoms of a carbocyclic aromatic compound by an O- or S-heteroatom including those heterocyclic compounds having five-membered rings which show aromatic characteristics—for example, pyran, thiophene, furan, benzothiophene and the like. Optional substitutents include one of more of halogen atoms having an atomic number of from 9 to 35, inclusive; or an alkyl, alkenyl or alkoxy group containing 1 to 6 carbon atoms, each optionally substituted by one or more halogen atoms; optionally substituted phenoxy, phenyl, benzyl or benzoyl and equivalent kinds of substituents.

In one embodiment, the alpha-hydroxynitrile has the formula II

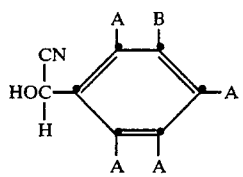

wherein each A is independently a hydrogen atom, a halogen atom having an atomic number of from 9 35, inclusive, or an alkyl, alkenyl or alkoxy group containing 1 to 6 carbon atoms, each optionally-substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; or is a group

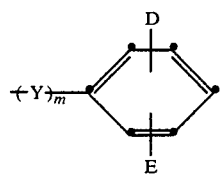

in which Y is O, CH$_2$, C(O); m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive.

Preferably, the optically-active alpha-hydroxynitrile products have the alpha-S-configuration when derived from aldehydes and, therefore, include S-alpha-hydroxynitriles of the formula III

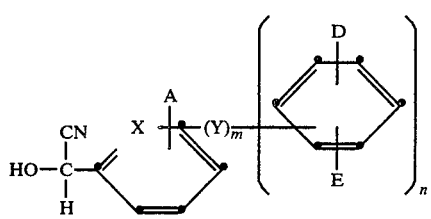

wherein n is 1; m is 0 or 1; Y is O, CH$_2$ C(O); A, D and E each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive. Preferably, Y is O. Preferably, A, D or E each independently is a hydrogen atom, a fluorine atom, a chlorine atom, a methyl group, a trifluoromethy group or a methoxy group. Preferably, one of D and E each is a hydrogen atom. An especially preferred embodiment of the alpha-S alpha-hydroxynitriles are those of the formula above in which D is a hydrogen atom and A and E each independently is a fluorine atom or a hydrogen atom, and preferably, when either A or E is fluorine, each is located at the 4-position of the ring relative to the benzyl carbon when A or relative to the Y=O bearing carbon atom when E. Especially suitable alcohols are when A is a fluorine atom at the 4-position and E is a hydrogen atom.

Non-limiting examples of alpha-hydroxynitriles of the formula I include
S-alpha-cyano-3-phenoxybenzyl alcohol,
S-alpha-cyano-4-fluoro-3-phenoxybenzyl alcohol,
S-alpha-cyano-3-(4-fluorophenoxy)benzyl alcohol, and the like.

In another embodiment of the process, the chiral cyanohydrin has the formula IV

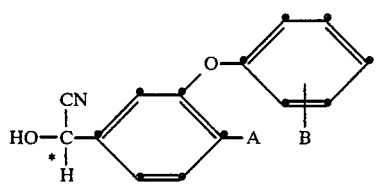

wherein * denotes an asymmetric carbon atom; and A and B each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive.

A further embodiment of the invention is directed to a process for increasing enantiomeric selectivity in chiral cyanohydrination of an aromatic aldehyde with hydrogen cyanide or a generator thereof in the presence of an inert, aprotic solvent and a chiral cyclo(-phenylalanylhistidine) catalyst, which process comprises the step of pretreating the aldehyde to remove catalyst poisons or impurities that adversely effect chiral selectivity.

A substantially water-immiscible, aprotic solvent for use in this invention is defined as an aprotic solvent in which the solubility in water is not more than 5% v, at the reaction temperature (and does not interfere with the reaction). For example, the solvent is a hydrocarbon, or ether solvent including acyclic, alicyclic or aromatic materials. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Useful ethers include diethyl ether, diisopropyl ether, methyl t-butyl ether and the like. Preferably, the solvent has a boiling point below about 150° C. Preferably, the solvent is an aromatic hydrocarbon, especially toluene, diisopropyl ether or diethyl ether or mixtures thereof (e.g. 25/75 of diethyl ether/toluene. Toluene gives especially high enantiomeric excess when the substrate is 3-phenoxybenzaldehyde. Advantages of diethyl ether are the higher rate of reaction and that the catalyst is not soluble and can be recovered as a solid at the end of the reaction.

The amount of catalyst can vary. For example, it can be used in the range of from about 0.1 to about 10 mole percent based upon the weight of the aldehyde present, especially about 1.0 to about 7.5 mole percent. The catalyst is preferably well dispersed in the reaction mixture.

The aromatic aldehyde reactant corresponds to the desired chiral cyanohydrin product, e.g., of formulas I, II, III or IV and preferably, is an aldehyde reactant of the formula V

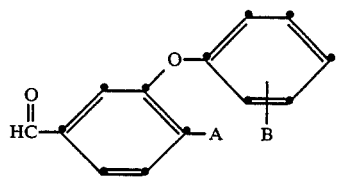

V wherein A and B have the same meanings as given in the formula IV above. Examples of suitable aldehydes of the formula above include 3-phenoxybenzaldehyde, 4-fluoro-3-phenoxybenzaldehyde, and the like.

The source of cyanide is hydrogen cyanide or an agent that generates hydrogen cyanide, under the reaction conditions. Hydrogen cyanide itself is preferred. The molar ratio of hydrogen cyanide to aldehyde is from about 1.0 to about 3.0 moles per mole of aldehyde and, preferably, from about 1.1 to about 2.0.

One embodiment of the present process is directed to use of a catalyst for cyanohydrination of aldehydes, comprising a solid chiral cyclo(phenylalanylhistidine) having a substantially noncrystalline component as disclosed in co-pending U.S. Ser. No. 535,500, filed Sept. 26, 1983 and its subsequent divisional applications, and U.S. Ser. No. 55,548, filed Nov. 14, 1983 as a continuation-in-part of U.S. Ser. No. 443,763, filed Nov. 22, 1982 (now abandoned) and also described below. The addition of some recycle chiral cyanohydrin product or other alcohol to the feed in chiral cyanohydrination is claimed in concurrently filed U.S. patent application Ser. No. 749,618 .

The catalyst can have a substantially amorphous or non-crystalline form. While the precise form of this cyclo(D-phenylalanyl-D-histidine) or cyclo(L-phenylalanyl-L-histidine) dipeptide is not known, it appears that the activated (amorphous or non-crystalline) form precipitated with a random structure and with a number of the available —NH groups in the dipeptide free of intermolecular hydrogen bonding to the available —C=O groups as compared with the less active (crystalline component form where the molecules had time to orient themselves as they were laid down into a highly-bonded orderly structure. Such being the case, the degree of amorphousness or non-crystallinity is most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu K$\alpha$ radiation (40KV, 35 ma).

The precent crystallinity was determined by a modified Hermans and Weidinger method (P. H. Hermans and A. Weidinger, *Makromol. Chem.*, 50, 98 (1961)). The diffuse background scattering below the main peaks was constructed with a consistent baseline between $5° \leq 2\theta \leq 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York (1974).

As used herein the terms "amorphous" or "non-crystalline" define active catalyst materials that have about 45% or more of an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres. Alternative methods to define amorphous and non-crystalline character are infrared or nuclear magnetic resonance spectral studies or observation of swelling of the material, e.g. in contact with the reactants of the cyanohydrination process.

In a preferred method, the dipeptide is prepared by the route described below in which HIS means histidine and PHE means phenylalanine.

Histidine O—Methylation

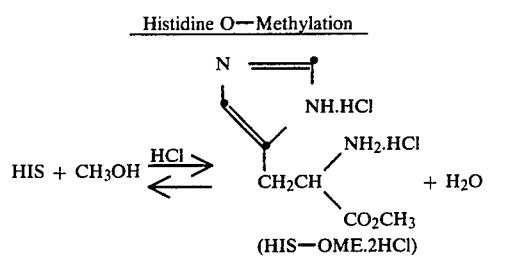

Leuchs' Anhydride Formation

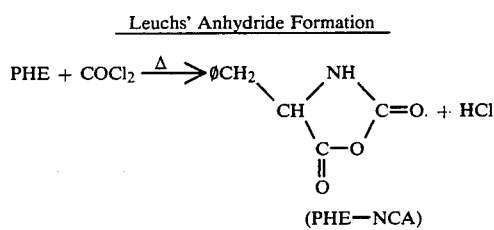

Coupling

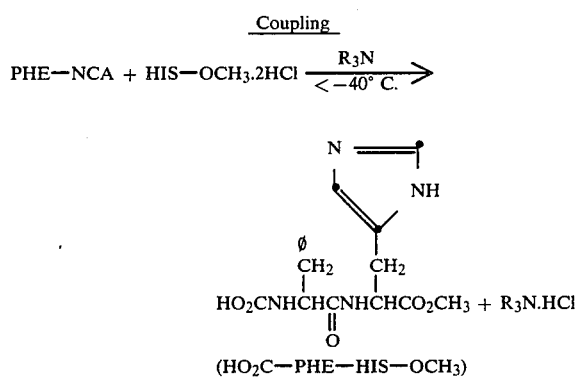

Carbamic Acid Decomposition

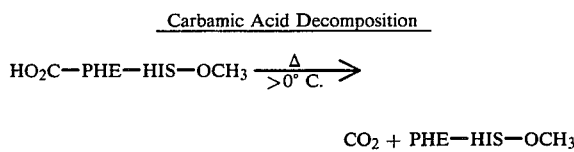

Cyclization

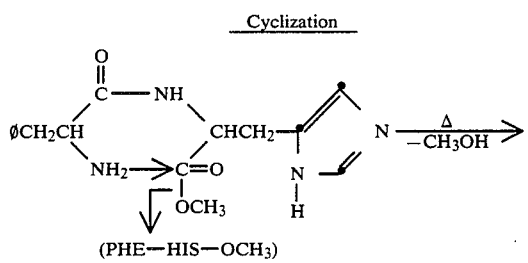

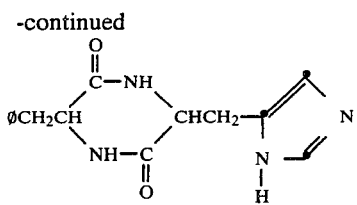

CYCLO (PHE—HIS)

When the catalyst is prepared as a solid, by conventional methods in the presence of water, it can also contain solvent (e.g. water) of crystallization and thus includes the presence or absence of solvent (e.g. water) of crystallization.

The solid catalyst can be recovered by extraction with acid followed by neutralization with a base, or preferably by treating with (dissolving in) a solvent, for example a hydroxylic solvent, including lower alkanols of 1 to 10 carbon atoms such as isopropanol or preferably methanol (preferably with heating, e.g. to reflux or quick flash), and reprecipitating (preferably below ambient temperature) to produce a less crystalline (or more amorphous) catalyst structure.

While it is preferred to directly prepare the catalyst used in the process of the present invention having the non-crystalline component, it is also possible to prepare a substantially crystalline catalyst and to subsequently activate the catalyst by converting at least part of the crystalline material to an amorphous form. Thus, the present invention is directed to both a method of directly preparing an active cyclo(D-phenylalanyl-D-histidine) or cyclo(L-phenylalanyl-L-histidine) dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming. It is believed that the breakdown of or the prevention of the formation of a number of intermolecular bonds between the amino N—H and the carboxyl C=O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or after treatment are within the scope of the invention. Among the illustrative examples of methods that reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The dipeptide catalyst recovered at the end of a conventional synthesis process is often almost completely inactive in the cyanohydrination reaction, apparently because it has become highly crystalline as can be determined by X-ray diffraction. Activation, as used herein, appears to involve converting at least part of the crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystallization cannot occur. There are a number of ways in which this might be effected: (a) rapid evaporation of the solvent, e.g. as in a spray dryer; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)-(d). Preferably, the method used is (a), rapid evaporation of the solvent and, especially, by means of spray drying.

Because of the polar nature and high melting point (~250° C) of the chiral cyclo(phenylalanylhistidine), the choice of solvents that will dissolve it to any appreciable extent is very limited. Potential solvents suitable and unsuitable that have been tested are listed in Table 1 in order of decreasing effectiveness, and the use of these will be discussed below in relation to the method of catalyst activation via recovery techniques or specific subsequent activation treatment.

TABLE 1
SOLVENTS TESTED FOR SOLUBILITY OF CYCLO(D-PHENYLALANYL-D-HISTIDINE)

| Solvent | B.P./°C. | Solvency |
|---|---|---|
| Dimethyl Sulfoxide | 189 | Good (5-10% w) |
| Acetic Acid | 118 | Good |
| Formamide | 210 | ≧2.3% at 25° C. |
| 1-Methyl-2-pyrrolidinone | 202 | ≧2.2% at 25° C. |
| Dimethylformamide | 153 | Fair to Good, <5% at 90° C. |
| Liquid Ammonia | −33 | ~2% at −40° C. |
| N—methylformamide | 185 | ≧2.4% at 25° C. |
| Acetonitrile | 80 | Fair to Poor, <<5% at 70° C. |
| Methanol | 64 | 1% w Hot, 0.3% w at 25° C. |
| Water | 100 | 1% at 75°, 0.2% at 25° C. |
| Acetone | 55 | Fair to Poor, <<1% at 25° C. |
| Liquid Carbon Dioxide | −78 | Poor, <0.2% at 25° C. |
| Carbon Disulfide | 45 | Very Poor |
| Diethyl Ether | 35 | Very Poor |
| Hydrocarbons | Var. | Very Poor |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C=O group, including ureas and aldehydes. Even by-product impurities of the dipeptide process containing such substituents are useful crystallization inhibitors, e.g. making an impure product can make a more active catalyst.

The reaction to prepare alpha-hydroxynitriles is suitably conducted by adding the aldehyde and solvent ot the chiral cyclo(phenylalanyl-histidine) catalyst, dispersing (mechanical grinding or agitating the mixture, e.g. by stirring), adding hydrogen cyanide and maintaining the reaction conditions for an amount of time to effect the formation of the optically-active alpha-hydroxynitrile. That is, preferably, the hydrogen cyanide is introduced concurrently with or subsequent to the solvent and/or aldehyde to increase the conversion and stereoselectivity. The presence of cyanide ions appears to have an adverse effect on the catalyst in this reaction. The forming and maintaining of a well dispersed but not necessarily homogeneous-like reaction mixture are useful. Separation and recovery of the optically-active ester product are achieved by conventional techniques, including extraction and the like.

The temperature of the reaction to prepare the optically active alpha-hydroxynitriles as well as the pressure can vary. At normal pressures, the temperature is from about −10° C. to about 80° C., more or less. Preferably, ambient temperatures of about 5° C. to about 35° C. are convenient to give good yield, rate of reaction and enantiomeric excess of the desired optically-active product, the lower temperature of about 5° C. giving good results.

The alpha-hydroxynitriles and their corresponding aldehydes are generally known in the literature. The S-benzyl alcohols are of interest per se or as intermediates to esters, e.g. of the pyrethroid type, for examle, S-alpha-cyano-3-phenoxybenzyl alcohol in U.S. Pat. No. 4,273,727.

The S-alpha-cyano-3-phenoxybenzyl alcohol or mixture enriched therein of the invention, is treated with a carboxylic acid halide, e.g., an S-alpha-isopropylphenylacetic acid chloride or an optionally-substituted chiral cyclopropanecarboxylic acid chloride, to give an optically-active cyanomethyl ester or amixture enriched therein. The cyanomethyl esters for which the optically-active form is prepared from one or more chiral cyanohydrins of the process of the invention, have e.g. the formula VI

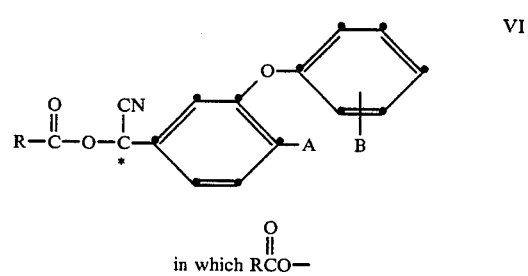

in which RCO— is the residue of a carboxylic acid of the pyrethroid type, which are generally known in the art, including in the optical forms, from e.g., U.S. Pat. Nos. 4,151,195, 4,239,737, 4,328,167 and 4,133,826, and British Pat. No. 2,014,137 and the like. Preferably, the product optically-active ester is S-alpha-cyano-3-phenoxybenzyl S-alpha-isopropyl (p-chlorophenyl)acetate, S-alpha-cyano-3-phenoxybenzyl S-alpha-isopropyl (p-(difluoromethoxy)phenyl)acetate, S-alpha-cyano-3-phenoxybenzyl (1R,cis)-3-(2,2-dichlorovinyl0-2,2-dimethylcycloproanecarboxylate, S-alpha-cyano-3-phenoxybenzyl (1R,cis)-3-(2,2-dibromovinyl)-2,2-dimethylcyclopropanecarboxylate, S-alpha-cyano-3-phenoxybenzyl (1R,cis)-3-(1,2-dibromo-2,2-dichloroethyl) -2,2-dimethylcyclopropanecarboxylate, S-alpha-cyano-3-phenoxybenzyl (1R,cis)-2,2-dimethyl-3-(neopentoxyiminomethyl)cyclopropanecarboxylate, and the like.

ILLUSTRATIVE EMBODIMENTS

The following embodiments are provided for the purpose of illustrating the invention and should not be regarded as limiting it in any way. The identity of the products was confirmed by infrared and nuclear magnetic resonance spectral analyses.

Embodiment 1

A Niro Atomizer laboratory spray dryer with a ca 31 inch diameter chamber was assembled. In operation, 40 SCFM $N_2$ is heated to 140° and fed to the dryer chamber. A warm solution of 0.5-1.0% w cyclo(D-phenylalanyl-D:histidine) in methanol is fed via a rotary vaned atomizer to the chamber above the $N_2$ inlet. The droplets of cyclo-(D-phenylalanyl-D-histidine) solution are rapidly dried to give hollow spherical particles of 1 to 10 μm diameter. The combined stream is fed to a cyclone where the particles are captured.

Seven test runs were made using 5 to 10 gm of cyclo (D-phenylalanyl-D-histidine) each. Starting with a catalyst that was inefficient for cyanohydrination, all the products were activated to give good reaction rate and produce (S)-alpha-cyano-3-phenoxybenzyl alcohol with EE's between 75-80% at 97% conversion of 3-phenoxybenzaldehyde. Water and sodium chloride, simulating recycle operation, apparently had no effect on activation. On the other hand, the addition of urea to further disrupt crystallization of cyclo (D-phenylalanyl-D-histidine) did not result in further improvement. The results of the seven test runs are tablulated in Table 2. Larger spray-dry experiments have given EE's of greater than 90%.

TABLE 2

ACTIVATION OF CYCLO(D-PHENYLALANYL-D-HISTIDINE) BY SPRAY DRYING

| Experiment | Catalyst Purity % w | Feed Composition (Rest MeOH) | | | | Feed Rate ml/min | $N_2$ Rate SCFM[f] | Temp In °C. | Temp Out °C. | Atomizer RPM × $10^{-3}$ | Catalyst Recovery % | Particle Size μm |
|---|---|---|---|---|---|---|---|---|---|---|---|---|
| | | DDCAT[d] % w | $H_2O$ % w | NaCl % w | Others % w | | | | | | | |
| 1 | 87 | 0.49 | | | | 115 | 42 | 135 | 60-75 | 37 | 46 | 1-12 |
| 2 | 87 | 0.48 | | | | 225 | 42 | ~160 | 60-70 | 31 | 58 | 1-12 |
| 3 | 92[b] | 0.84 | | | | 125 | 43 | 135-140 | 55-65 | 37 | 66[a] | 1-10 |
| 4 | 92[b] | 0.63 | 4.5 | | | 110 | 43 | 139 | 65-75 | 36 | 56[a] | 1-10 |
| 5 | 92[b] | 0.62 | 4.5 | 1.0 | | 135 | 43 | 137-140 | 55-65 | 36 | 68 | 1-10 |
| 6 | 92[b] | 0.65 | — | — | 0.033 | 125 | 43 | 139 | 70-75 | 36 | 58 | 1-10 |
| 7 | 92[b] | 0.80 | — | — | — | 135 | 42 | 135-140 | 55-70 | 38 | 77 | 1-10 |

| | | Cyanohydrination In Toluene at 25° C. | |
|---|---|---|---|
| Experiment | Time hr | POAL[e] Conversion % | (S)—POAL:CN[e] Selectivity[c] % |
| 1 | 1 | 92.2 | 91 |
| | 2 | 95.9 | 90 |
| | 4 | 96.9 | 90 |
| | 5.5 | 95.9 | 90 |
| 2 | 1 | 91.3 | 90 |
| | 3 | 95.5 | 88 |
| | 4 | 96.7 | 88 |
| | 5.1 | 98.4 | |
| 3 | 1 | 93 | 90 |
| | 2 | 96.7 | 90 |
| | 3 | 96.6 | 92 |
| | 4 | 97.6 | 90 |
| 4 | 1 | 94.6 | |
| | 2 | 96.9 | 90 |
| | 3 | 98.7 | 89 |
| 5 | 1 | 93.6 | 91 |
| | 2 | 96.6 | 90 |
| | 3 | 95.4 | 91 |
| | 4 | 97.5 | 90 |
| | 5 | | 90 |
| 6 | 1 | 92.3 | 90 |
| | 2 | 91.0 | 90 |
| | 4 | 94.7 | 89 |
| | 5 | 96.0 | 90 |
| 7 | 1 | 93.3 | 93 |
| | 2 | 96.1 | 91 |
| | 3 | 95.9 | 92 |
| | 4 | 97.6 | 92 |

TABLE 2-continued

ACTIVATION OF CYCLO(D-PHENYLALANYL-D-HISTIDINE) BY SPRAY DRYING

| | | | 5 | 96.0 | 91 |

[a] Mostly held in cyclone by static electricity.
[b] 96% purity by potentiometric titration.
[c] EE = 2 (selectivity) - 100, %.
[d] DDCAT = cyclo(D-phenylalanyl-D-histidine)
[e] POAL = 3-phenoxybenzaldehyde, (S)—POAL.CN = (S)—α-cyano-3-phenoxybenzyl alcohol.
[f] SCFM = standard cubic feet per minute.

Embodiment 2

Another method tested for activating the catalyst is freeze drying. This approach requires a solvent for the dipeptide that freezes at a convenient temperature and is volatile enough to be evaporated at below that temperature and at a practical pressure (vacuum). Of the solvents tested, only water and acetic acid meet these requirements. The results of some of these tests are summarized in Table 3. Freeze drying of a 0.1% w solution of the dipeptide in water gave an excellent product (Experiment 5). An attempt to freeze dry a solution in dimethyl sulfoxide failed because the solvent was too high boiling to be evaporated at about 0° C. and 170 microns pressure. Solutions in glacial acetic acid were readily freeze dried. The product from this freeze drying contains one mole of acetic acid per mole of catalyst. In spite of this, the product was surprisingly active and selective (Experiment 2). This acid is relatively loosely held by the catalyst, and it was volatilized away in a sweep of air, on the one hand (Experiment 3), or neutralized by triethylamine treatment, on the other (Experiment 4). In both cases the products had about the same activity (conversion/selectivity: 93%/72%.

TABLE 3

ACTIVATION OF CYCOL(D-PHENYLALANYL-D-HISTIDINE) BY FREEZE DRYING

| | | Cyanohydrination[b] | |
|---|---|---|---|
| Experiment | Solvent/Work Up | Conversion %/3 Hr | Enantiomeric Excess, %[a] |
| 1 | From 2% solution in dimethyl sulfoxide | — | — |
| 2 | From 1.9% solution in acetic acid | 74 | 56 (6.5) |
| 3 | Product from experiment 2 air swept 2 days | 93 | 73 (5) |
| 4 | From 0.1% solution in water | 98 | 85 (2.5) |

[a] Numbers in parentheses indicated time, in hours.
[b] Cyanohydrination of 3-phenoxybenzaldehyde with HCN to give (S)—alpha-cyano-3-phenoxybenzyl alcohol.

Embodiment 3

Acid treatments of 3-phenoxybenzaldehyde (POAL) were conducted as described below.
1. A sample of POAL was extracted with 1.9% w aqueous HCl. Phase separation was very poor. After withdrawing upper aqueous layer, water was added for repeat extraction. The water was removed and the POAL was sparged with $N_2$ until it became clear (dried). Phase ratios were not measured. The amines orginally present were reduced from ca 0.2% w to ca 0.01% w.
2. A 20.6% w POAL in toluene was extracted with roughly an equal volume of 1.9% w aqueous HCl. After phase separation to remove the lower aqueous layer, the hazy upper layer was sparged with $N_2$ until it cleared. Toluene was added to bring the POAL concentration back to 20.6% w. Residual amines were undetectable (<0.01% w) in the solution.

The treated 3-phenoxybenzaldehyde was then subjected to chiral cyanohydrination by treating a 20.6% w solution of the aldehyde in toluene with hydrogen cyanide in the presence of cyclo(D-phenylalanyl-D-histidine) catalyst. Results of the chiral cyanohydrination to produce S-alpha-cyano-3-phenoxybenzyl alcohol are set forth in Table 4 below.

TABLE 4

| CHIRAL CYANOHYDRINATION OF 3-PHENOXYBENZALDEHYDE | |
|---|---|
| Aldehyde Treatment | % S—alcohol Product |
| 1 | 91 |
| 2 | 91 |

Embodiment 4

A solution of 20.6% w of 3-phenoxybenzaldehyde in toluene was treated with dilute sulfuric acid at a ratio of 30:1 organic phase to acid phase. The resulting mixture was vigorously agitated and then centrifuged to effect clean phase separation to remove basic nitrogen compounds, including amines, in the acid fraction. Results of chiral cyanohydrination with 3-phenoxybenzaldehyde showing the effect of reduced total basic nitrogen in cyclo(D-phenylalanyl-D-histidine) catalyst are set forth in Table 5 below.

TABLE 5

| EFFECT OF $H_2SO_4$ TREATMENT OF 3-PHENOXYBENZALDEHYDE USED IN CHIRAL CYANOHYDRINATION | | |
|---|---|---|
| Experiment | TBN[a] p.p.m. | % Product S—alcohol |
| 1 | 48 | 85 |
| 2 | 40 | 88 |
| 3 | 17.5 | 88 |
| 4 | 4 | 89 |
| 5 | 4 | 91 |
| 6 | 3 | 91 |
| 7 | 2.5 | 90 |
| 8 | 2 | 90.3 |
| 9 | 2 | 92.2 |

[a] TBN means total basic nitrogen compounds present in 3-phenoxybenzaldehyde.

What is claimed is:

1. A process for the preparation of a chiral aromatic cyanohydrin or a mixture enantiomerically enriched therein which comprises treating an aromatic aldehyde in an inert, aprotic solvent with hydrogen cyanide or a generator thereof in the presence of a cyclo(D-phenylalanyl-D-histidine) or cyclo(L-phenylalanyl-L-histidine) dipeptide catalyst and pretreating the aldehyde or solution thereof in the solvent with an acid or acidic-acting material to remove basic nitrogen compound catalyst posions or impurities which adversely effect enantiomeric selectivity.

2. A process according to claim 1 wherein the solvent is an aromatic hydrocarbon, an ether or mixtures thereof.

3. A process according to claim 2 wherein a mineral or organic acid is used.

4. A process according to claim 3 wherein the chiral cyanohydrin product is an S-cyanohydrin of formula IV

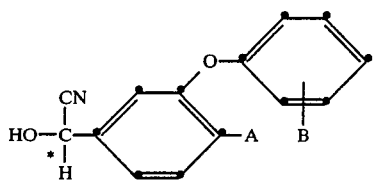

wherein * denotes an asymmetric carbon atom; and A and B each independently is a hydrogen atom, a halogen atom having an atomic number of from 9 to 35 inclusive, or an alkyl or alkoxy group containing 1 to 6 carbon atoms, each optionally substituted by one or more halogen atoms having an atomic number of from 9 to 35, inclusive, or a mixture enriched therein.

5. A process according to claim 4 wherein a mineral acid is used.

6. A process according to claim 5 wherein the chiral cyanohydrin is S-alpha-cyano-3-phenoxybenzyl alcohol.

7. A process for increasing enantiomeric selectivity in chiral cyanohydrination of an aromatic aldehyde with hydrogen cyanide or a generator thereof in the presence of an inert, aprotic solvent and a cyclo (D-phenylalanyl-D-histidine) or cyclo(L-phenylalanyl-L-histidine) dipeptide catalyst which process comprises the step of pretreating the aldehyde or a solution thereof in the solvent with an acid or acidic-acting material to remove basic nitrogen compound catalyst poisons or impurities that adversely effect enantiomeric selectivity.

8. A process according to claim 7 wherein the solvent is an aromatic hydrocarbon, and ether or mixtures thereof.

9. A process according to claim 7 wherein a mineral or organic acid is used.

10. A process according to claim 7 wherein the chiral cyanohydrin product is an S-cyanohydrin of formula IV

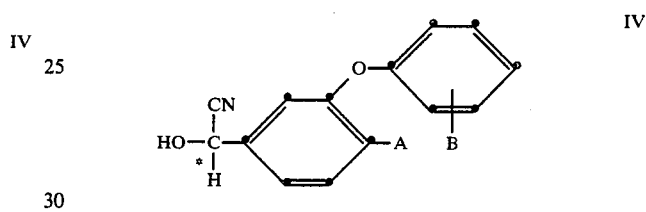

wherein * denotes an asymmetric carbon atom; and A and B each independently is a hydrogen atom, a halogen atom having an atomic number of from 9 to 35 inclusive, or an alkyl or alkoxy group containing 1 to 6 carbon atoms, each optionally substituted by one or more halogen atoms having an atomic number of from 9 to 35, inclusive, or a mixture enriched therein.

11. A process according to claim 10 wherein the chiral cyanohydrin is S-alpha-cyano-3-phenoxybenzyl alcohol.

* * * * *